US00PP24462P3

(12) United States Plant Patent
Austin

(10) Patent No.: US PP24,462 P3
(45) Date of Patent: May 20, 2014

(54) SHRUB ROSE PLANT NAMED 'AUSCHRIS'

(50) Latin Name: *Rosa hybrida*
Varietal Denomination: AUSchris

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 126 days.

(21) Appl. No.: 13/506,557

(22) Filed: Apr. 27, 2012

(65) Prior Publication Data

US 2013/0263333 P1 Oct. 3, 2013

(30) Foreign Application Priority Data

Apr. 3, 2012 (EP) ..... 2012/0765

(51) Int. Cl.
*A01H 5/00* (2006.01)

(52) U.S. Cl.
USPC ..... Plt./102

(58) Field of Classification Search
USPC ..... Plt./130, 138, 141, 149, 102, 107
See application file for complete search history.

*Primary Examiner* — Howard Locker
(74) *Attorney, Agent, or Firm* — KPPB LLP

(57) ABSTRACT

A variety of rose plant of the shrub class, named 'AUSchris'. The 'AUSchris' rose is a plant bred for cut-flower production with an unusually long vase life, long elegant magenta pink buds with petals that deepen as they age taking on hints of purple, and a balanced pure rose fragrance with hints of raspberry, red currant, geranium and bergamot that remain through all stages of the flowering.

1 Drawing Sheet

Classification: The present invention relates to a new *Rosa hybrida* of the market class 'English Rose'.

Variety denomination: The new plant has the varietal denomination 'AUSchris.'

CROSS-REFERENCE TO RELATED APPLICATIONS

The current application claims priority to a European Community Plant Variety Application No. 2012/00765, filed Apr. 3, 2012, the disclosure of which is incorporated herein by reference.

ORIGIN OF INVENTION

This invention relates to a new and distinct variety of shrub rose plant named 'AUSchris', which was originated from the cross-pollination of the two 'unnamed' seedlings of *Rosa hybrida.*

BACKGROUND OF THE INVENTION

The primary objective of this breeding was to produce a variety of rose bred for cut-flower production with an unusually long vase life, long elegant magenta pink buds with petals that deepen as they age taking on hints of purple, and a balanced pure rose fragrance with hints of raspberry, red currant, geranium and bergamot that remain through all stages of the flowering.

SUMMARY OF THE INVENTION

Among the features which distinguish the new variety from other presently available and commercial rose cultivars known to the inventor is the following combination of characteristics: a magenta pink color that fades into a deeper almost purple color with age, a fragrance that remains throughout all stages of life, and a pure rose fragrance with hints of raspberry, red currant, geranium and bergamot.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUSchris' may be asexually propagated by budding. The budding successfully occurred on the plant/rootstock *Rosa* cv. 'Inermis'.

COMPARISON WITH PARENTS

The seed and pollen parents of 'AUSchris' are two unnamed seedlings. The new rose may be distinguished from its seed parent, by the following combination of characteristics: the new variety is deep pink fading to purple with fewer petals and slightly large flowers, whereas the seed parent is dark red with a smaller bloom and more petals. The new rose may be distinguished from its pollen parent, by the following combination of characteristics: the pollen parent is white, with a hybrid tea form.

COMPARISON WITH THE CLOSEST COMMERCIALLY AVAILABLE CULTIVAR

The closest commercially available cultivars to the new variety are the 'AUSglade' (U.S. Plant Pat. No. 19,161). The new rose may be distinguished from the 'AUSglade variety by the following combination of characteristics: the 'AUSchris' has 65 petals whereas 'AUSglade' has 140-150; 'AUSchris' has a shallower cup, which is rosette shaped, whereas 'AUSglade' has a deep cupped and quartered bloom form.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSchris' specimens were made at a nursery in Albrighton, Wolverhampton, United Kingdom. The following description is of 1 year-old rose plants of the new variety grown indoors in a greenhouse in Albrighton, Britain in the month of October. Phenotypic expression may vary with environmental, cultural and climatic conditions, as well as differences in conditions of light and soil.

FLOWER CHARACTERISTICS

Blooming habit: Continuous. The number of stems per plant during the growing season is 0.8 stems per plant per month.

Bud:

- *Size*.—About 4 cm long and 3 cm in diameter when the petals start to unfurl.
- *Form*.—The bud form is long and pointed ovoid.
- *Color*.—When sepals first divide, the bud color is red RHS N66A. When half blown, the upper sides of the petals are RHS 67A and the lower sides of the petals are RHS 67A.
- *Sepals*.—Arrangement: Regular. Color: Upper Surface: Green RHS 138A. Lower Surface: green RHS 138D in middle with RHS 138B outer. Length: 4 cm. Width: 1 cm. Shape: Lanceolate. Surface texture: Upper Surface: Smooth. Lower Surface: Downy. Number: There are 3 normally appendaged sepals, and 2 unappendaged sepals with hairy edges.
- *Receptacles*.—Color: green RHS 144A. Shape: Funnel. Size: Medium, about 1.2 cm×1.2 cm. Surface: Smooth.
- *Peduncle*.—Length: short, averaging about 5 cm. Surface: Smooth. Color: light green RHS 144A. Strength: Strong.

Blooms:

- *Size*.—Large, average open diameter is about 10 cm.
- *Borne*.—Singly during commercial production with disbudding, or in clusters of 1 to 4 blooms without disbudding.
- *Stems*.—Strength: Strong, average length is about 80 cm. Diameter: 5 mm.
- *Form*.—When first open, bloom is cupped. Permanence of bloom: flattens.

Petalage: Number of petals under normal conditions: 65.

- *Color*.—The upper sides of the petals are purple RHS 67A. The reverse sides of the petals are RHS N66A, and the base of the petals is yellow-orange RHS 14A.
- *Variegations*.—None.
- *Discoloration*.—When sepals first divide, the bud color is red RHS N66A fading to purple RHS 67A as they age.
- *Fragrance*.—Slight. Character of fragrance: pure rose with hints of raspberry, red currant, geranium and bergamot.

Petals:

- *Texture*.—Velvety.
- *Size*.—Width: 4.3 cm. Length: 5.1 cm.
- *Surface*.—Rough.
- *Shape*.—Deltoid.
- *Margin*.—Entire but slightly frilly edge.
- *Apex shape*.—Rounded but undulating.
- *Base shape*.—Obtuse.
- *Form*.—Tips slightly recurved.
- *Arrangement*.—Imbricated.
- *Petaloids*.—Number: 3. Color: RHS N66A. Length: 25 mm×10 mm. Shape: Half-moon. Margin: Irregular.
- *Persistence*.—Petals hang on and dry.
- *Lastingness*.—On the plant: About 8-10 days. As a cut flower: About 8-10 days.

Reproductive parts:

- *Stamens*.—Number: 250. Length: 6 mm.
- *Anthers*.—Length: 3 mm. Color: RHS 21A. Arrangement: regular around styles.
- *Filaments*.—Color: Yellow RHS 21A. Length: 3 mm.
- *Pollen*.—Color: gold yellow RHS 21A.
- *Pistils*.—Number: 70. Length: 6 mm.
- *Styles*.—Color: Pale pink RHS 48D. Length: 5 mm (medium).
- *Stigmas*.—Color: Clear yellow RHS 12A. Length: 1 mm.
- *Hips*.—None Observed.

PLANT CHARACTERISTICS

Plant form: Shrub.

Plant growth: Vigorous.

Age to maturity: One years.

Mature plant:

- *Height*.—1.3 m.
- *Width*.—0.75 m.

Rootstock: *Rosa* cv. 'Inermis'.

Foliage:

- *Size*.—Medium, about 16 cm long×12 cm wide for a compound leaf with 5 leaflets.
- *Quantity*.—Normal. Number of leaves per flowering stem is: 12.
- *Color*.—New foliage: Upper side: light green RHS 144A with hints of greyed red RHS 178A at the margins. Lower side: green RHS 144B. Mature foliage: Upper side: dark green RHS 136A. Lower side: green RHS 137B.

Leaflets:

- *Number*.—Leaflets on normal mid-stem leaves is: a mixture of 5 and 7.
- *Size*.—About 7.3 cm long×4.5 cm wide for a terminal leaflet.
- *Shape*.—Broadly ovate.
- *Base shape*.—Rounded.
- *Apex shape*.—Acuminate.
- *Texture*.—Leathery.
- *Finish*.—Upper surface is glossy.
- *Edge*.—Serrated.
- *Serrations*.—Single.
- *Petiole*.—Color: Green RHS 144A with greyed red RHS 178A. Length: 3.5 cm. Width: 2 mm. Surface Texture: Glandular.
- *Petiole rachis*.—Color: green RHS 144A with greyed red RHS 178A on upperside. Underside: Smooth.
- *Stipules*.—Length: 2.2 cm, smooth and glandular. Color: RHS 144A.
- *Auricle*.—Shape: Sword-shaped. Length: 6 mm. Width: 0.75 mm. Color: RHS 144A.
- *Vein color*.—Same as leaf, RHS 135A with RHS 178A.
- *Venation pattern*.—Net-veined (reticulate).

Wood:

*New wood*.—Color: Greyed-red RHS 178A. Bark: Smooth.

*Old wood*.—Color: Dark-green RHS 136A. Bark: Smooth.

Branching habit:

*Number of lateral branches*.—Few.

*Lateral branch dimensions*.—Length: 50 cm. Diameter: 6 mm.

Stems:

*Mature stem*.—Length: 130 cm. Diameter: 7 mm.

*Internode distance*.—Average: typical is 6 cm.

*Stem pubescence present*.—No.

Prickles:

*Quantity*.—On main canes from base: Ordinary. Number per stem length: 13 per 15 cm. On laterals from main canes: Ordinary. Number per stem length: 13 per 15 cm.

*Form*.—Deep concave.

*Length*.—5-6 mm×3-4 mm.

*Color when young*.—Red RHS 178B.

*Color when mature*.—Brown RHS 166C.

Small prickles:

*Quantity*.—Main stalk: Few. Laterals: Few.

Disease resistance:

*Mildew*.—Resistant.

*Blackspot*.—Not tested.

*Rust*.—Not tested.

Pest resistance: Not tested.

Winter hardiness: Not tested.

Growing conditions: Normal greenhouse conditions.

What is claimed is:

1. A new and distinct variety of cut rose plant suitable for luxury cut flower production, substantially as herein shown and described.

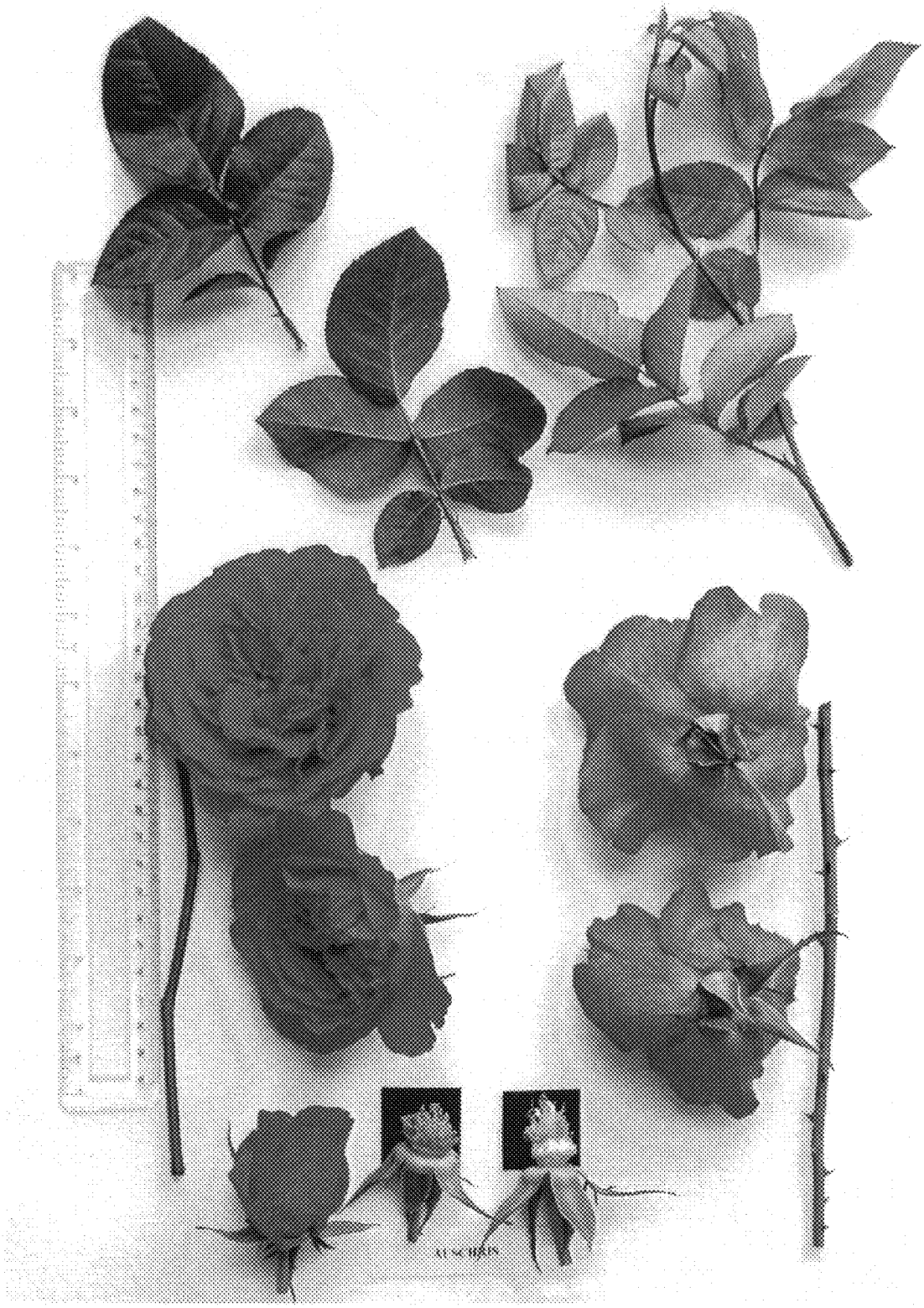

* * * * *